(12) United States Patent  (10) Patent No.: US 9,376,131 B2
Lenkman et al.  (45) Date of Patent: Jun. 28, 2016

(54) MODULAR CART (71) Applicant: Sightpath Medical, LLC, Bloomington, MN (US)

(72) Inventors: Thomas Lenkman, Saint Charles, MO (US); David Massey, Saint Charles, MO (US)

(73) Assignee: Sightpath Medical, LLC, Bloomington, MN (US)

( * ) Notice: Subject to any disclaimer, the term of this patent is extended or adjusted under 35 U.S.C. 154(b) by 0 days.

(21) Appl. No.: 14/289,281

(22) Filed: May 28, 2014

(65) Prior Publication Data

US 2015/0344054 A1  Dec. 3, 2015

(51) Int. Cl.
*B62B 3/04* (2006.01)
(52) U.S. Cl.
CPC .................................. *B62B 3/04* (2013.01)
(58) Field of Classification Search
CPC ...... B62B 2206/04; B60P 7/08; B60P 7/0807
USPC ............................ 280/47.34, 79.11, 79.3, 761
See application file for complete search history.

(56) References Cited

U.S. PATENT DOCUMENTS

| | | |
|---|---|---|
| 1,804,542 A | 5/1931 | Perin |
| 2,172,154 A | 9/1939 | Perin |
| 2,599,170 A | 6/1952 | Franks |
| 3,022,028 A | 2/1962 | Reinhard et al. |
| 3,125,035 A | 3/1964 | Loomis |
| 3,296,981 A | 1/1967 | Bergstrand |
| 3,318,611 A | 5/1967 | Branning |
| 3,962,660 A | 6/1976 | Duckett |
| 4,237,794 A | 12/1980 | Biaggini et al. |
| 4,457,551 A * | 7/1984 | Anthony .................... 296/65.04 |
| 4,660,796 A | 4/1987 | Garrec |
| 4,755,089 A | 7/1988 | Ellgass |
| 4,934,720 A | 6/1990 | Dobron |
| 5,032,045 A | 7/1991 | Calco |
| 5,149,030 A | 9/1992 | Cockrill |
| 5,497,708 A | 3/1996 | Jeruzal |
| 5,845,914 A * | 12/1998 | Lenkman ................... 280/43.17 |
| 6,006,676 A | 12/1999 | Creek et al. |
| 6,099,220 A | 8/2000 | Poth |
| 6,286,805 B1 | 9/2001 | Bunn et al. |
| 6,769,368 B2 | 8/2004 | Underbrink et al. |
| 6,843,625 B2 * | 1/2005 | Hewitt ............................. 410/66 |
| 7,066,102 B1 * | 6/2006 | Tossavainen ............... 114/230.1 |
| 7,077,067 B2 | 7/2006 | Bodde et al. |
| 7,736,104 B2 | 6/2010 | Hobson |

* cited by examiner

*Primary Examiner* — Bryan Evans
(74) *Attorney, Agent, or Firm* — Husch Blackwell LLP

(57) ABSTRACT

A modular cart for transporting and securing femtosecond lasers and other highly sensitive equipment to medical facilities by truck transit and within medical facilities by rolling the modular cart is disclosed. The modular cart includes a cart base member with rollers, a sub plate attached to the top portion of the cart base member, a control box attached to a top end portion of the cart base member, and an adaptable interface plate attached thereto the top portion of the sub plate for selectively receiving and securing highly sensitive equipment. The adaptable interface plate may be modified by size, shape, and receiving means in order to receive and secure various specific types of highly sensitive equipment. Different adaptable interface plates may be used for receiving and securing different highly sensitive equipment.

18 Claims, 10 Drawing Sheets

MODULAR CART

BACKGROUND OF INVENTION

The present invention relates to a portable cart for transporting highly sensitive equipment, such as a femtosecond laser. The invention includes the ability to secure the portable cart in a truck bed or other transportation means for transport to various locations and subsequent removal of the portable cart with the highly sensitive equipment for delivery to a doctor's office or clinic to use and operate the equipment as desired.

Femtosecond lasers have been used recently in cataract surgery because the lasers can generate consistent and stable incisions. The lasers present an alternative to previous methods including using sharp, sterile blades to cut the cornea. Using such blades can increase the risk of infection following surgeries. Meanwhile, using the femtosecond laser may reduce the aforementioned risk of infection. Also, femtosecond lasers may be used in other optical surgeries including "FemtoLASIK" surgery. As a result of their safety and efficacy, femtosecond lasers have become a common and effective instrument in ophthalmology. Presently, a number of femtosecond lasers are at or near the point of commercial release including the Alcon LenSx, OptiMedica Catalys, LensAR, and Technolas laser systems.

Due to the size and highly sensitive nature of femtosecond lasers, as well as other highly sensitive lasers for ophthalmic surgery, fixed-site centers where femtosecond lasers are permanently located are typically employed only in large metropolitan areas. Of course, this limits the availability of the femtosecond lasers to large segments of users in outlying geographic areas.

As a result, a self-contained portable cart for transporting highly sensitive equipment such as that shown in U.S. Pat. No. 5,845,914 ("the '914 patent") was developed. This portable cart is able to securely and safely transport highly sensitive equipment from one location to another using an air cushion suspension system. Air cushions contained in a mobile cart act as shock absorbers for when the cart and its highly sensitive equipment are in transit. Multiple carts securing highly sensitive equipment may be secured within a truck cab or other transportation means. The cart of the present invention may be removably mounted to the floor of the truck cab to prevent the cart and highly sensitive equipment from jostling therein and damaging the equipment.

In the prior art portable cart, however, the frames and components associated with the highly sensitive equipment are not adaptable such that the carts may be used with any type of laser or other highly sensitive equipment that comes to market. The frames are not capable of receiving and securing multiple sizes and varieties of highly sensitive equipment. As technology evolves, and subsequent lasers and other highly sensitive equipment are developed, it would become expensive to be required to replace the entire cart each time such a development emerged. A solution is needed where the cart may be adaptable to transport and secure lasers and other highly sensitive equipment that have a variety of shapes and sizes.

Moreover, the cart of the '914 patent includes two apparatuses extending upward from the cart for housing controls, compressors, and other electronic or mechanical devices for controlling the cart. The presence of both apparatuses may cause the weight of the cart of the '914 patent to be imbalanced. Thus it would be advantageous to secure some of the cart's electrical and mechanical components in a more centered, balanced position.

The cart from the prior art '914 patent also includes a mechanism for locking the cart down in a truck cab where the cart is housed and transported from one location to another. In the prior art reference, the mechanism is driven by a power activated retractable arm or pin that engages a floor support of the truck. The power activated mechanism eliminates the requirement of manually releasing the retractable arm from the support. Yet, in the event of a power failure, unloading the carts from a truck cab can become difficult without damaging a cart, floor support, retractable arm, or the truck cab floor. Thus a manual means for releasing the retractable arm or pin from the floor support is desired.

Moreover, in the cart claimed in the '914 patent, the cart bearing the highly sensitive equipment could be weighted unevenly such that it unnecessarily shifts in transit in the truck cab or other storage facility. Thus a solution is desired where the weight imbalance of the equipment is taken into account. In the solution, the cart and highly sensitive equipment would further be cushioned in a manner to prevent damage to the highly sensitive equipment.

SUMMARY OF INVENTION

The present invention relates to a modular cart for securely and stably transporting highly sensitive equipment. In the present invention, a novel modular cart includes a cart base member with wheels attached thereto for mobility and various components included therein that facilitate operation of the cart. Some of the components included within the cart base member are air cushions that act as shock-absorbers for when the cart is in motion, an air compressor for expanding and contracting the air cushion, and a mechanism for securing a cart and its highly sensitive equipment in a truck cab. The cart base member may further have mounted above and at one of its end portions a control box for containing therein various electronics and backup batteries. A sub plate is mounted to the top portion of the cart base member. The sub plate includes a plurality of through holes for being secured to the cart base member. A second plate, an adaptable interface plate is further mounted on top of the sub plate. The adaptable interface plate includes a first group of apertures sized, positioned and located for selective mating to the sub plate. The adaptable interface plate may include a second group of apertures sized, positioned, and located for selective mating with mating components of highly sensitive equipment such as a femtosecond laser. Thus a plurality of interface plates may be manufactured for mating with and securing a plurality of types of highly sensitive equipment.

In operation, the same modular cart may be used to transport multiple types of highly sensitive equipment. To do so, the interface plate that corresponds to a specific piece of highly sensitive equipment must be used.

The adaptable interface plate of the present invention further comprises removable screw feet used to lift the adaptable interface plate and the highly sensitive equipment above it off the ground such that the cart base member and sub plate may be removed from under the adaptable interface plate. Thus while the interface plate and highly sensitive equipment are temporarily or permanently stationed in a doctor's office, surgical room, or other location, the cart base member and sub plate may be used again to transport a separate piece of highly sensitive equipment.

A support frame member mounted to the truck cab floor further secures the cart and equipment by receiving a power activated retractable arm or pin associated with the cart base member. The power activated retractable arm of the present invention further comprises a manual release lever for quickly releasing the pin from the support frame member such that the cart and equipment may be removed from the truck cab floor in the event of a power failure.

The adaptable interface plate further may comprise a removable stabilizer bar which is mounted to and extends from a rear side portion thereof. When the modular cart transporting the highly sensitive equipment is in transit via a truck cab, the stabilizer bar is positioned and located for attachment to a cushioned stabilizer. The cushioned stabilizer is mounted to the truck cab floor and sized and positioned to bear an imbalanced portion of the weight of the cart and equipment associated therewith.

DETAILED DESCRIPTION

The following detailed description illustrates the invention by way of example and not by way of limitation. This description will clearly enable one skilled in the art to make and use the invention, and describes several embodiments, adaptations, variations, alternatives and uses of the invention.

The modular cart of the present invention is designed for use with a femtosecond laser or other highly sensitive equipment and is further designed to securely and stably transport the femtosecond laser or other highly sensitive equipment in transit to a doctor's office, surgical room, or other location, or within a truck cab for delivery to one of the aforementioned locations. Moreover, the modular cart described herein may be used with a plurality of laser or highly sensitive equipment types. The method in which the present invention operates and is constructed will become apparent from the description that follows.

Figure 1:
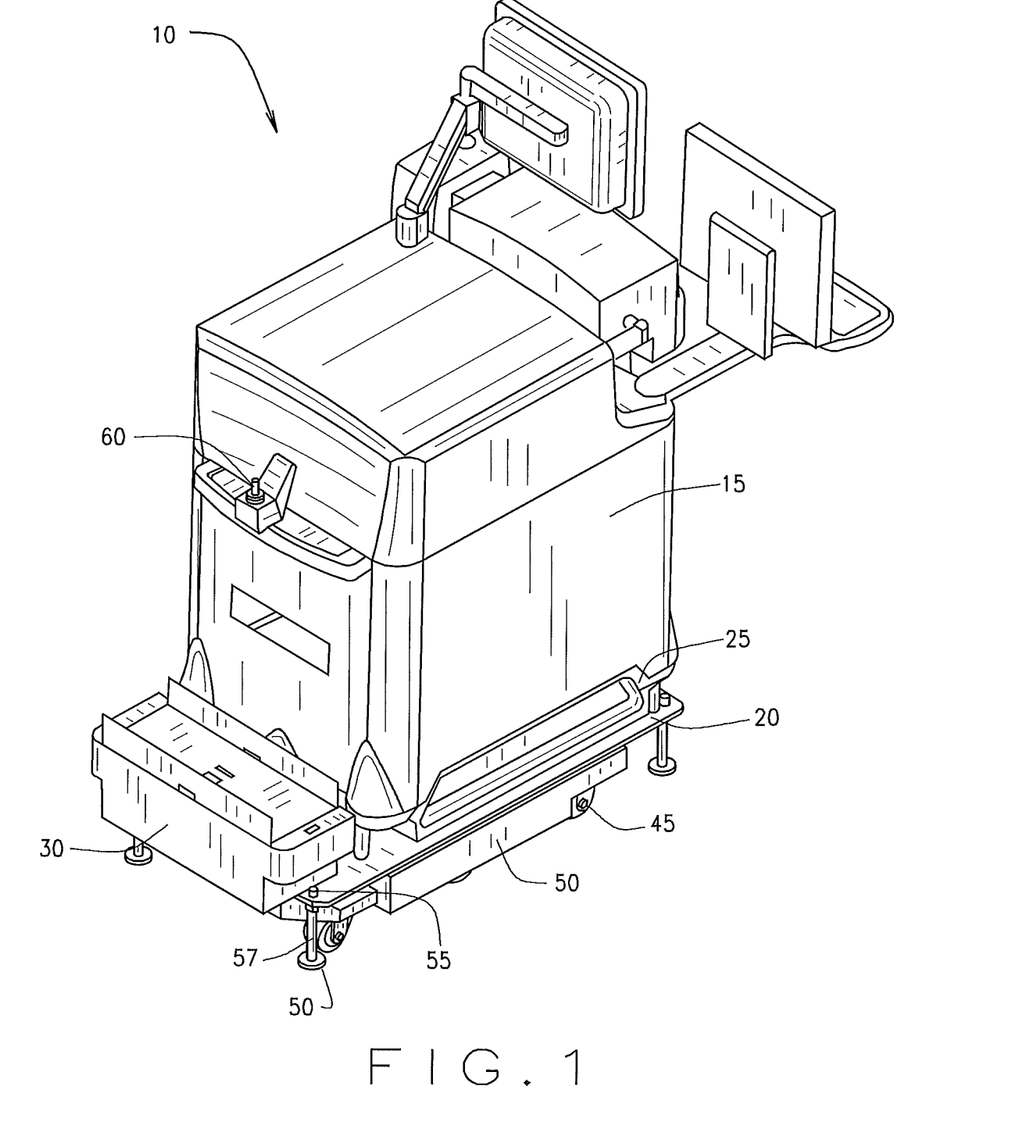
FIG. 1 illustrates a perspective view of one embodiment of a modular cart and highly sensitive equipment mounted thereon, the modular cart constructed and assembled according to the teachings of the present invention.
Figure 2:
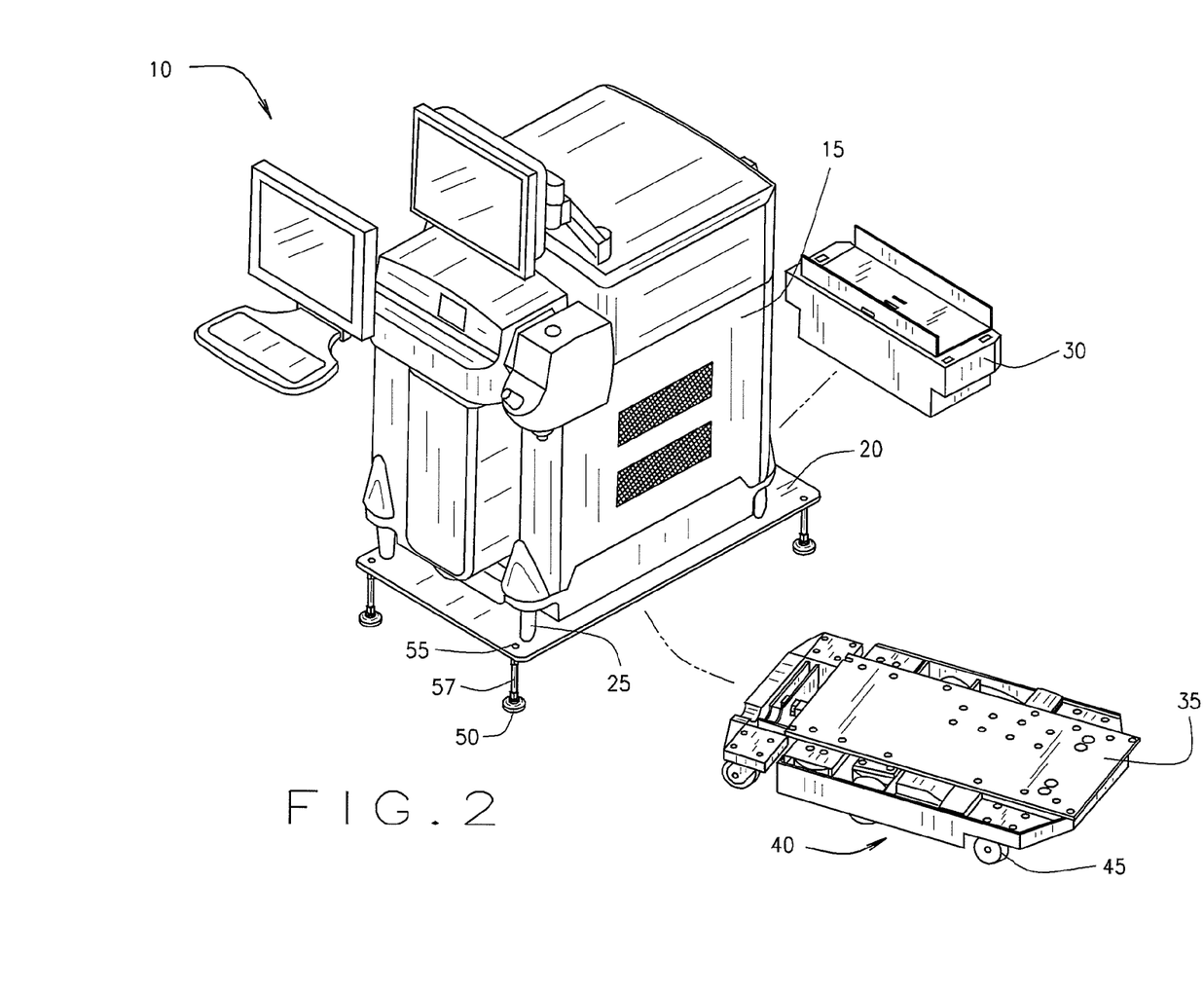
FIG. 2 illustrates an exploded view of the modular cart and highly sensitive equipment of FIG. 1.

Referring to the drawings more particularly by reference numbers, wherein like numerals refer to like parts, the number 10 in FIG. 1 identifies a modular cart constructed according to the teachings of the present invention. FIG. 2 illustrates the modular cart 10 and its components described herein below in an exploded view. The modular cart 10 may be used to transport a medical device, for example a femtosecond laser. In FIG. 1, the device supported by cart 10 is an ophthalmological device 15. Specifically, device 15 in the illustrated embodiment is a femtosecond laser, though other embodiments are contemplated and described herein below where device 15 is a different medical device needing to be securely and stably transported. The device 15 is releasably mounted to an adaptable interface plate 20. Adaptable interface plate 20 includes rods 25 that are received by cavities (not illustrated) positioned and located on the underside of device 15 for releasably yet securely mounting device 15 to interface plate 20. Interface plate 20 further may include a control box 30 attached thereto for containing a plurality of functional components. For example control box 30 may include electronics for operating the cart 10, spare batteries, or other components. When the device 15 is mounted to the interface plate 20 via rods 25, device 15 is sufficiently mounted thereto to allow the cart 10 to be wheeled around and transported.

The top surface of a sub plate 35, as illustrated in FIG. 2, may be releasably mounted to the bottom surface of the interface plate 20. The plates 20, 35 may be mounted by a screw mechanism, a friction fit, or other foreseeable stable, but releasable, attachment means. The bottom surface of the sub plate 35 may be releasably mounted to the top surface of a cart base member 40. The cart base member 40 preferably includes a powered drive system and a plurality of functional components such as air bladders an air compressor, and other components in the cart of the '914 patent. In operation, the cart 10 acts as an adaptable means for transporting highly sensitive equipment, such as device 15.

Sub plate 35 is configured specifically to selectively mate on its bottom surface with cart base member 40. In the present embodiment the bottom surface of sub plate 35 is bolted to cart base member 40. The top surface of sub plate 35 is configured specifically to selectively mate with adaptable interface plate 20 in a manner described in greater detail herein below. While the specific means by which the sub plate 35 may mount to the cart base member 40 and interface plate 20 may vary, the sub plate 35 will be configured to mate with the aforementioned components specifically.

Adaptable interface plate 20 is configured specifically such that its bottom surface will selectively mate with the top surface of sub plate 35. However, the configuration for attachment with the top surface of adaptable interface plate 20 varies depending on the highly sensitive device to be transported. Similarly to the sub plate 35, while the means by which the interface plate 20 may selectively mate with the sub plate 35 may vary, the bottom surface of interface plate 20 will be configured to mate with the sub plate 35 specifically. Also, the means by which the interface plate 20 selectively mates with highly sensitive equipment may vary, but the top surface of interface plate 20 will be configured to mate with a specific highly sensitive equipment. The mechanisms by which the plates 20 and 35 mate with other components are discussed in greater detail herein below.

The cart base member 40 includes wheels 45 for facilitating the movement of the cart 10 and transporting a medical device such as device 15. Apertures 55 of the adaptable interface plate 20 receive and secure removable screw feet 50 and legs 57 associated therewith. In transit, as illustrated in FIG.

1, removable screw feet 50 are in the "up" position such that they do not interfere with wheels 45.

When the cart 10 and device 15 have been moved to a desired location, removable screw feet 50 are extended downwardly such that the feet 50 contact the ground. Thus, the cart 10 and the weight of the various components and devices associated therewith are supported by the feet 50 in contact with the ground. Once the screw feet 50 have been extended downwardly such that they are in contact with the ground, the cart base member 40 may be rolled away from under the cart 10 such that the cart base member 40 may be used with another device 15 or other highly sensitive equipment. The cart base member 40 removed from under the interface place 20 and the removable screw feet 50 in the "down" position is illustrated in FIG. 2.

The removable screw feet 50 may be selectively moved to and from the "up" and "down" positions, respectively, by manipulating legs 57. In the embodiments illustrated in FIGS. 1 and 2, the legs 57 include threaded portions for mating with threaded portions within apertures 55 such that when the legs 57 are screwed appropriately they move upwardly within aperture 55 and extend upwardly therefrom as illustrated in FIG. 1. Legs 57 may also be screwed such that they move downwardly within aperture 55 and extend downwardly therefrom, as illustrated in FIG. 2. When legs 57 are extended fully downward, cart base member 40 may be removed from under the cart 10 such that a device may be semi-permanently or permanently positioned in a clinic or other surgical center. In alternative embodiments, legs 57 may be telescoping, or they may be movable by other means presently known or foreseeable to those skilled in the art.

The cart 10 and device 15 may include various functional components known to those skilled in the art. For example, the cart 10 and device 15 may include a joystick 60 for operatively controlling the movement of the cart 10. The joystick 60 may be in electronic and/or data communication with the cart 10. The connections associated therewith may be housed within control box 30. Joystick 60 allows an operator to reduce the physical effort he or she must exert in transporting the cart 10 as it is moved throughout a facility or even within a vehicle such as a truck.

Figure 3:
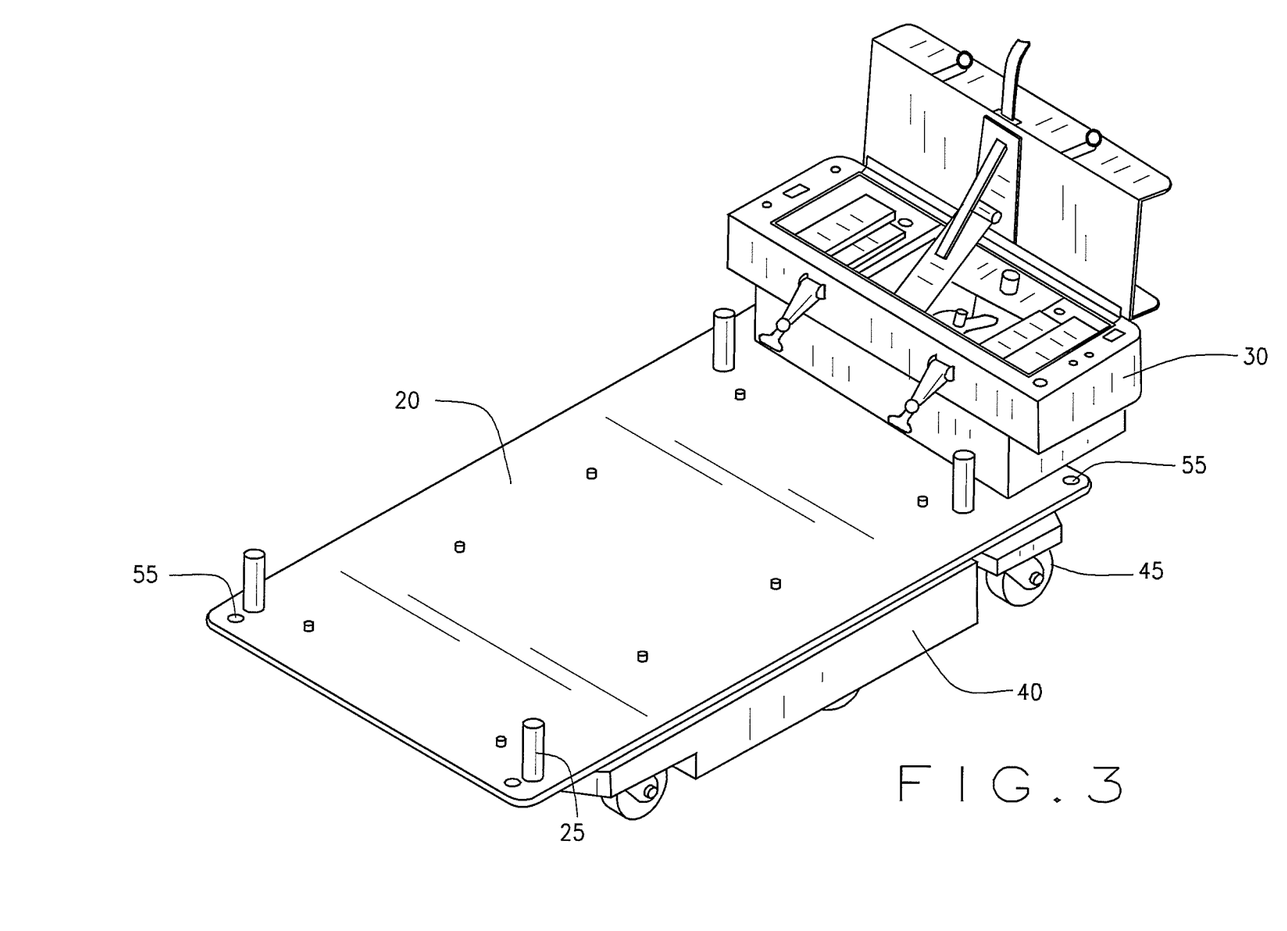
FIG. 3 illustrates a perspective view of a cart base member and adaptable interface plate mounted thereon.

FIG. 3 illustrates cart base member 40 with adaptable interface plate 20 mounted thereon. Rods 25 may be inserted into cavities (not illustrated) positioned and located on the underside of device 15 and in substantial alignment with rods 25. The rods 25 and cavities may be selectively engageable with one another via a friction fit. Alternatively the device 15 may be selectively engageable with interface plate 20 by a different attachment mechanism, for example a screw assembly, latch system, or other mechanism known or foreseeable in the art. In FIG. 3, control box 30 for containing a number of components for use therewith is illustrated. Apertures 55, through which removable feet 50 and legs 57 may be received and secured are further illustrated.

Figure 4:
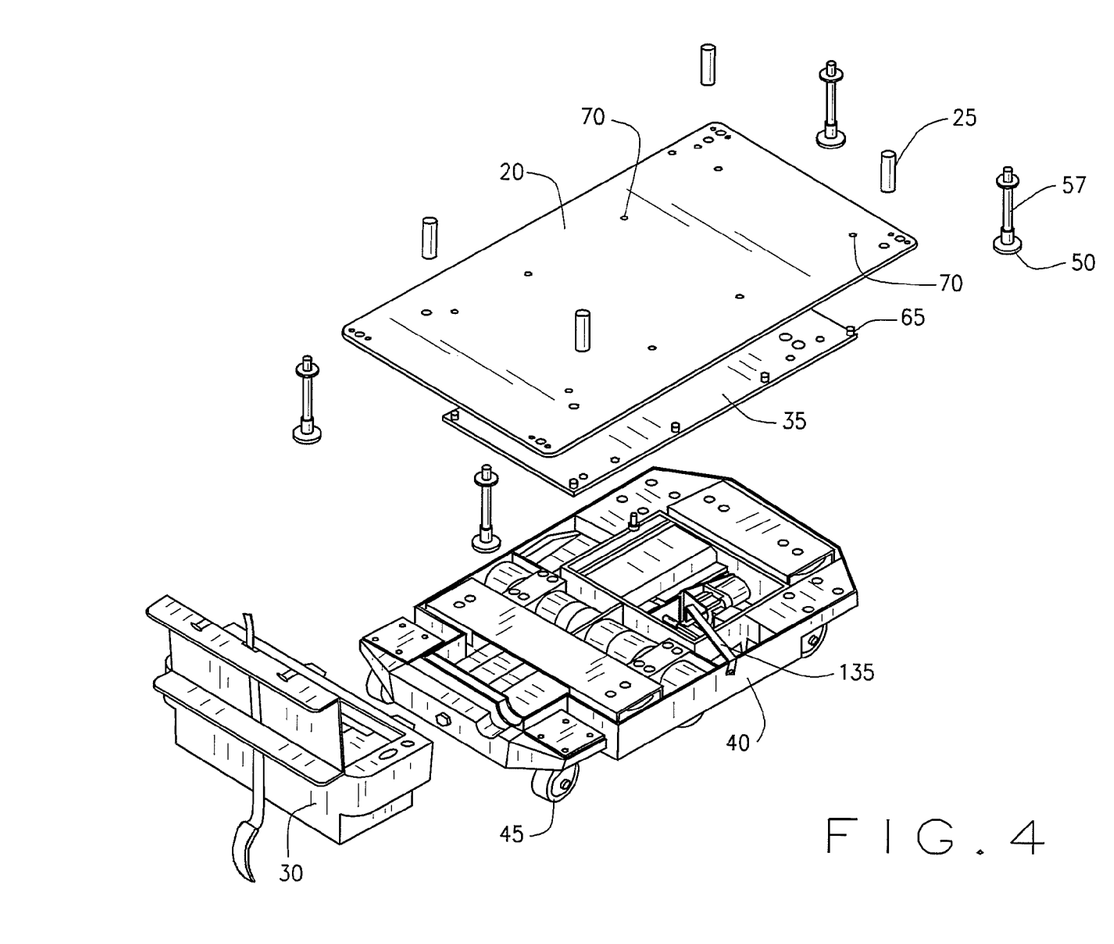
FIG. 4 illustrates an exploded view of the cart base member, a sub plate, and the adaptable interface plate of FIG. 3.

FIG. 4 illustrates in greater detail the means by which the present invention is assembled. Cart base member 40 may be selectively engaged with the adaptable interface plate 20 via rods 65 associated with sub plate 35. In the illustrated embodiment, rods 65, which may be in substantial alignment with apertures 70 of the interface plate 20, are the specific means by which the sub plate 35 may be selectively engaged with the interface plate 20. As previously mentioned, the means by which the sub plate 35 and adaptable interface plate 20 are selectively engaged may be in the aforementioned manner, or alternatively it may be by friction fit or other foreseeable attachment means.

Figure 5:
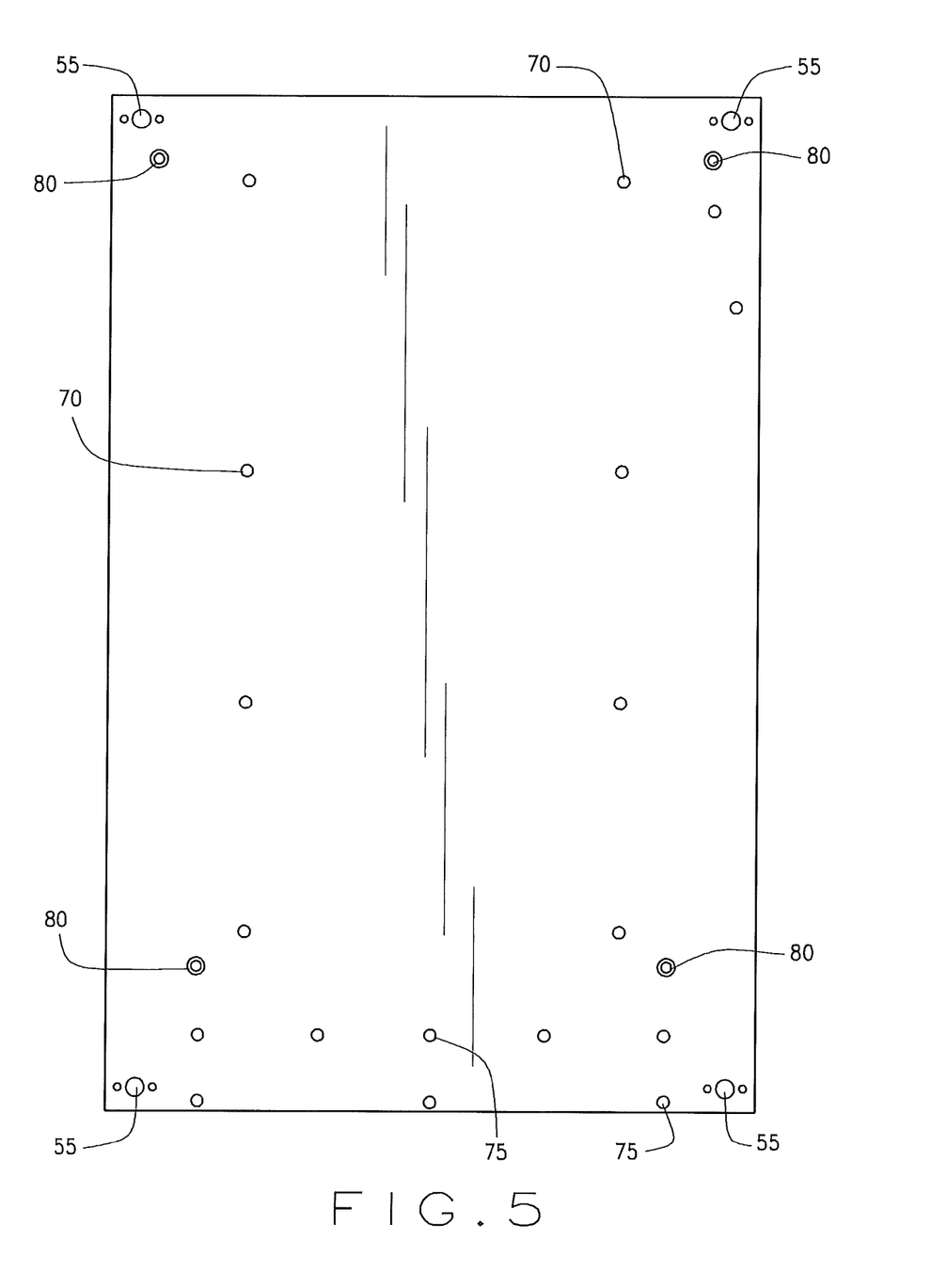
FIG. 5 illustrates a top plan view of the adaptable interface plate of FIGS. 3 and 4.

FIG. 5 illustrates a top perspective view of adaptable interface plate 20 for selective engagement with sub plate 35 at its bottom surface and device 15 at its top surface. The illustrated adaptable interface plate 20 includes apertures that are specifically positioned and located for selective engagement with device 15. Moreover, the illustrated interface plate 20 includes apertures 75 for further securing control box 30 to the interface plate 20 by attachment means substantially similar to those discussed herein and known in the art.

It should be noted that an alternative interface plate may be used for transporting highly sensitive equipment different than device 15. In such an alternative embodiment, the interface plate would include apertures 70 for receiving and securing sub plate 35, and it would include apertures 55 for receiving and securing removable screw feet 55 and legs 57 associated therewith. It would further include apertures 75 for selective engagement with the control box 30.

Adaptable interface plate 20 for securing device 15 includes apertures 80. Apertures 80 are sized and shaped specifically for receiving and securing rods 25. Rods 25 may be secured within apertures 80 by a threading mechanism, or they may be secured simply by a friction fit. The rods 25 are sized and shaped for being received by cavities (not illustrated) of the underside of device 15 specifically. Adaptable interface plate 20 includes apertures 80 because it is manufactured for use with device 15 only. If an adaptable interface plate were manufactured for use with highly sensitive equipment different than device 15, the alternative interface plate would include an attachment means for selectively engaging that particular highly sensitive equipment which may include differently sized, shaped, and/or positioned apertures, or it may be selectively attachable with highly sensitive equipment in a manner discussed herein, known in the art, or foreseeable to those skilled in the art.

Figure 6:
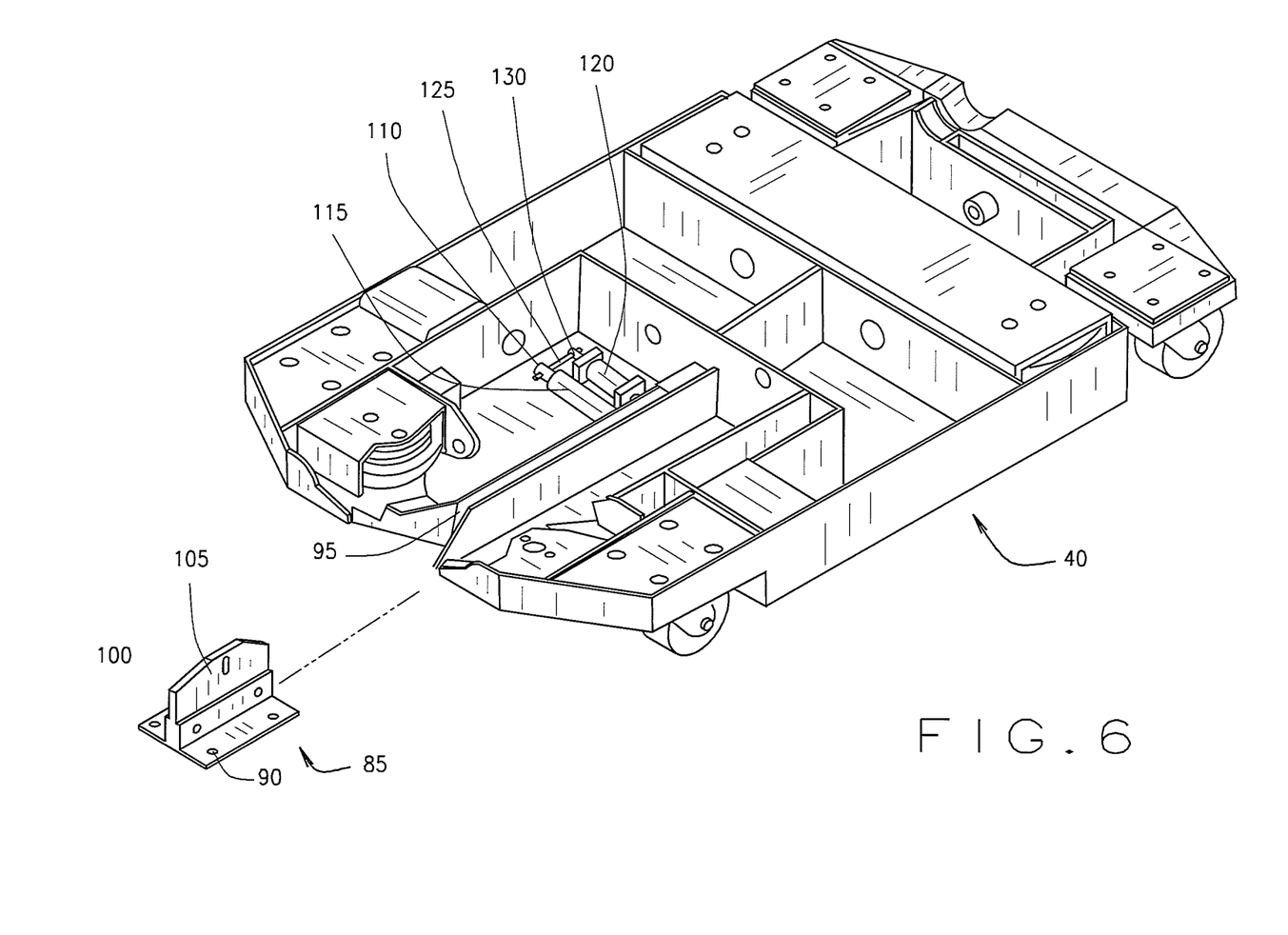
FIG. 6 illustrates an exploded view of a support frame member aligned for being received by a support frame member.

Cart 10 may be transported within a truck or other transportation means for transporting the cart 10 and highly sensitive equipment such as device 15. FIG. 6 illustrates a support frame member 85 receiving cart base member 40, which when used functionally may include sub plate 35, adaptable interface plate 20, and device 15 mounted thereon (not illustrated). Support frame member 85 is illustrated as an isolated component in FIG. 6, but in operation, it may be selectively mounted to the floor of a truck trailer, storage warehouse or other surface where carts 10 and highly sensitive equipment associated therewith is stored. Support frame member 85 includes a plurality of through holes 90 for receiving bolts for attaching the frame member 85 to a floor surface. Other means of securely attaching the support frame member 85 are contemplated herein.

A channel 95 extends through the front portion of cart base member 40 of a width sufficient for receiving a ridge 100 of the frame member 85. As such when the cart base member 40 and its components associated therewith are being transported, a means of securing the cart 10 and device 15 is provided. When the cart base member 40 approaches frame member 85, channel 95 receives ridge 100 of frame member 85. Frame member 85 may slide rearwardly into the channel 95 until it abuts the cart base member 40 where the channel 95 stops (not illustrated). When frame member 85 is abutting the end portion of channel 95, receiving eyelet 105 of frame member 85 is in substantial alignment with a pin 110 housed within a barrel cylinder 115. The pin 110 extends through the cylinder 115 and has a friction fit within the cylinder 115 such that the pin 110 may slide within cylinder 115 when a force is applied to it, but the pin 110 does not slide within cylinder 115 if a force is not applied to it. Typically the pin 110 is controlled via a powered mechanism discussed herein below.

Figure 7:
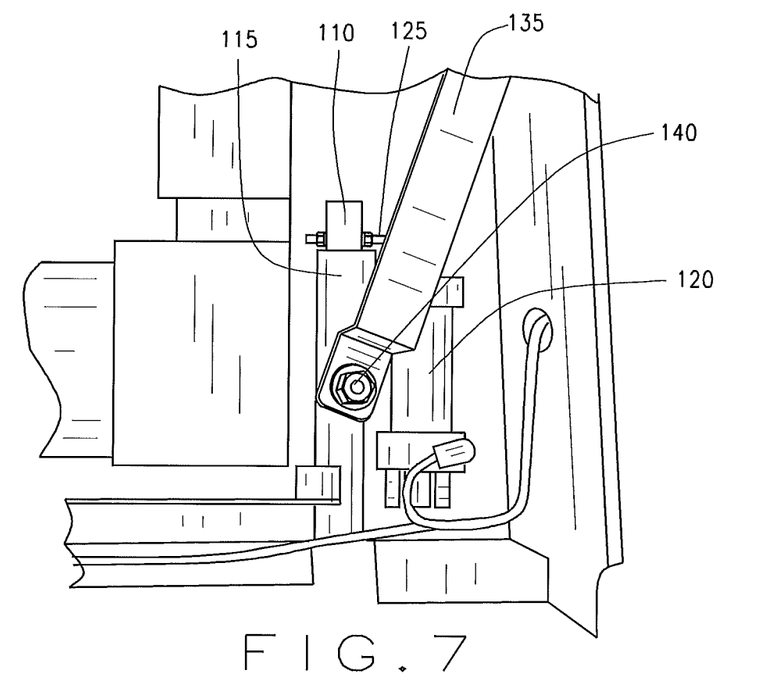
FIG. 7 illustrates an enlarged partial top plan view of a power activated retractable arm and manual release lever of the cart base member.
Figure 8:
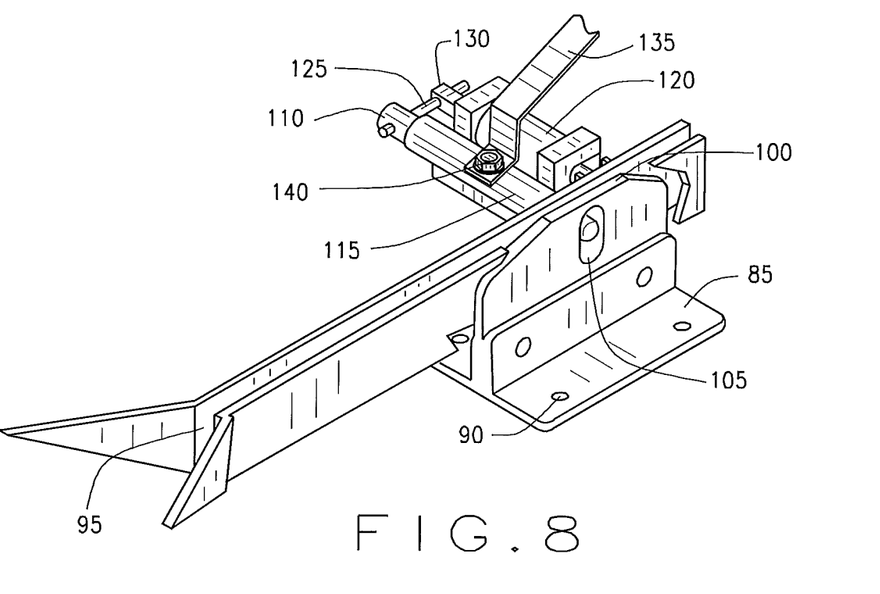
FIG. 8 illustrates a partial perspective view of the power activated retractable arm and manual release lever of the cart base member when selectively engaged with the support frame member.

FIGS. 7 and 8, along with FIG. 6 illustrate the powered mechanism. A pneumatic actuator 120 located adjacent the cylinder 115 and associated therewith is located within cart base member 40. Pneumatic actuator 120 may be controlled via electronics and air supply means associated with actuator 120 and not illustrated in the figures provided. Pneumatic actuator 120 is in mechanical communication with pin 110 via attachment rod 125. When the pneumatic actuator 120 is activated via the aforementioned electronics and air supply means which may be contained in control box 30, air is injected into the actuator which drives a piston to compress a spring contained within actuator 120. When the spring is compressed, rod 130 associated with actuator 120 and connected with attachment rod 125 is forced outwardly. This outward force is consequently applied to pin 110 within cylinder 115. As a result, pin 110 is further removed from eyelet 105. The manner by which the actuator 120 functions is known in the art, and the actuator 120 and the components contained therein are commercially available.

Thus the pin 110 may be power-activated to be inserted into eyelet 105 in order to be secured to frame member 85 and consequently a floor surface, or it may be power-activated in order to be removed from eyelet 105 to release the pin 110 from the eyelet 105 and consequently a floor surface. The locking mechanism formed by the pin 110 and eyelet 105 may be used in loading and unloading carts 10 including highly sensitive equipment. In alternative embodiments the powered mechanism described above may not be pneumatic and may be otherwise hydraulically, mechanically, or otherwise controlled.

In a typical scenario, the pin 110 may engage the frame member 85 via eyelet 105 or disengage therefrom via the powered mechanism described above. Yet, if power fails, a manual release mechanism for releasing the pin 110 from eyelet 105 is herein provided. A handle 135, a portion of which is illustrated in FIGS. 7 and 8, and the entirety of which is illustrated in FIG. 4, may further be attached to the cylinder 115. In the illustrated embodiment, handle 135 is attached to the cylinder 115 by a bolt 140. At its other end, handle 135 may be attached to a side portion of the cart base member 40 such that when the manual release mechanism is not needed, handle 135 is out of the way. Handle 135 may be attached to a side portion of the cart base member 40 as illustrated in FIG. 4. The bolt 140 extends downwardly through cylinder 115 where it is further attached to pin 110.

In operation, in the event of a power failure or other event necessitating the manual release of a cart 10 from frame member 85, handle 135 may be unattached from the side portion of cart base member 40. Handle 135 may then be turned and pulled in a forward direction, in the direction away from aperture 105 of frame member 85. When the handle 135 is pulled away from the aperture 105, bolt 140 attached to pin 110 causes pin 110 to be pulled away therefrom also. It should be noted that cylinder 115 including pin 110 therein also is pulled away in the direction of the applied force. As a result, pin 110 may be removed from aperture 105 and frame member 85, allowing cart 10 to be disengaged from frame member 85 and thus being removable therefrom.

Figure 9A:
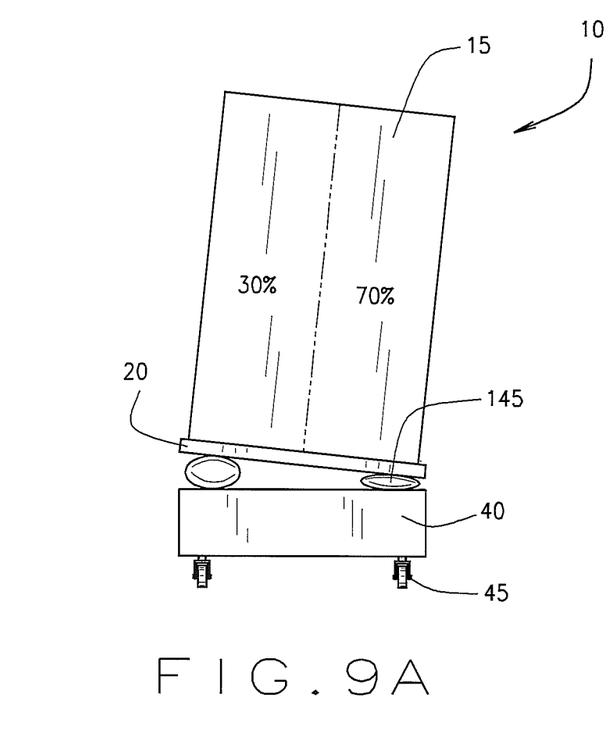
FIG. 9A illustrates a rear elevation view of an unevenly distributed load on the modular cart.

Highly sensitive equipment such as device 15 associated with cart 10 may be imbalanced. The equipment may include a number of components that are heavy, and those components may not necessarily be evenly distributed within highly sensitive equipment such as device 15. FIG. 9A broadly illustrates the consequences of such an imbalance. Device 15 in the illustrated embodiment includes 70% of its weight on one side and 30% of its weight on an opposite side in the example embodied in FIG. 9A. As such, air bladders 145 positioned and located between interface plate 20 and cart base member 40 for absorbing shock when highly sensitive equipment is in transit may have uneven weights applied to them. Further, as illustrated in FIG. 9A, the uneven weight could cause highly sensitive equipment such as device 15 to lean to one side or another. In transit, this can cause unintended consequences including damage to equipment such as device 15.

Figure 9B:
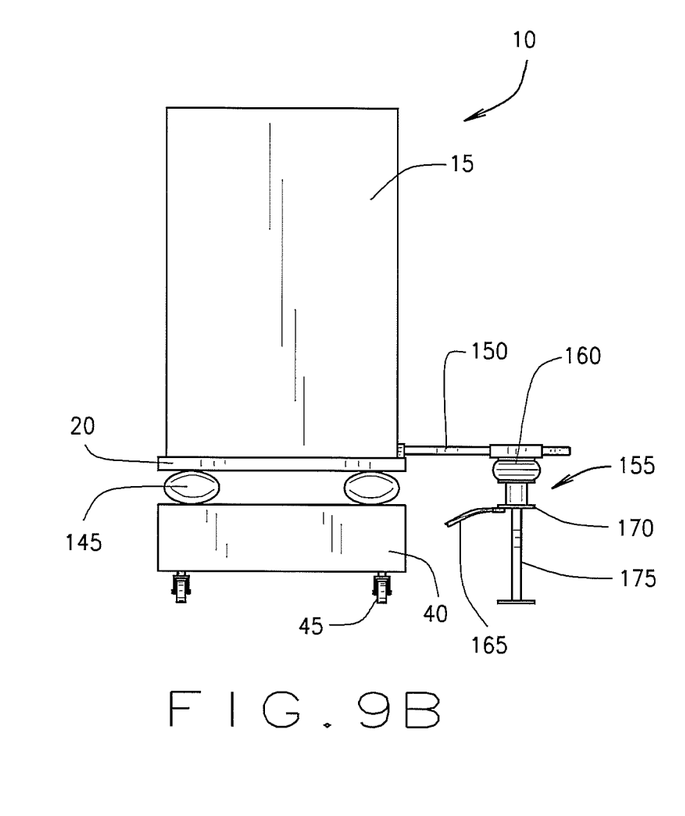
FIG. 9B illustrates a rear elevation view of a modular cart selectively engaged with a cushioned stabilizer.
Figure 10:
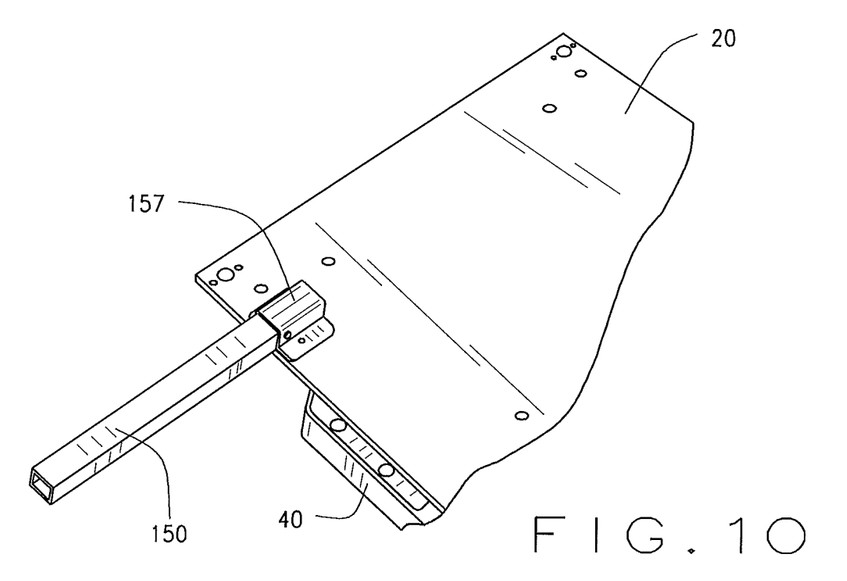
FIG. 10 illustrates a partial perspective view of a stabilizer bar attached to the adaptable interface plate of FIG. 5.

Aimed at reducing the weight imbalance during transit, a mechanism including a stabilizer bar 150 and a cushioned stabilizer 155 is illustrated in FIG. 9B. The stabilizer bar 150 and cushioned stabilizer 155 are illustrated in greater detail in FIGS. 10 and 11. A bracket 157 may be used to attach stabilizer bar 150 to adaptable interface plate 20. Other means known in the art or that are foreseeable may be used for attaching stabilizer bar 150 to interface plate 20 or an alternative interface plate for use with highly sensitive equipment other than device 15, as described above.

Figure 11:
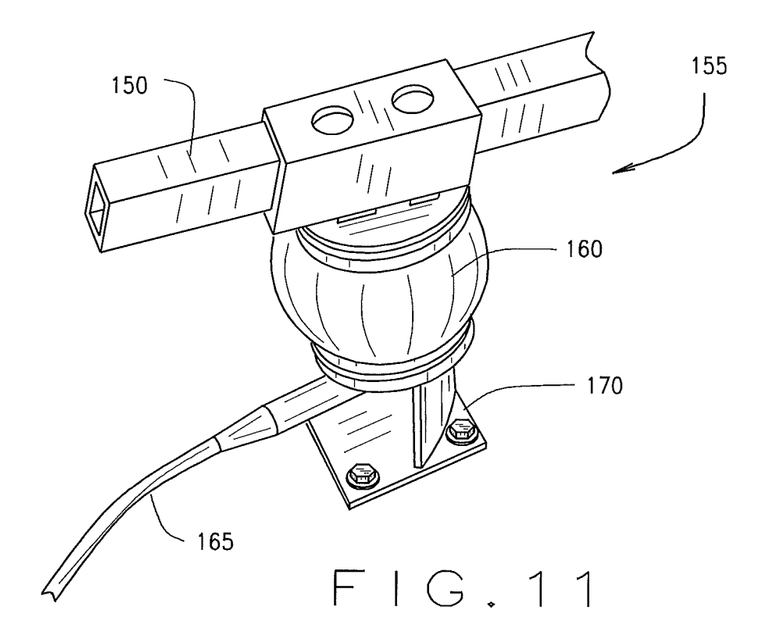
FIG. 11 illustrates an enlarged perspective view of the cushioned stabilizer of FIG. 9B.

Meanwhile cushioned stabilizer 155 may receive stabilizer bar 150 in order to support the imbalanced weight of device 15 or other highly sensitive equipment. Cushioned stabilizer 155 may include an air bladder 160 for absorbing some of the impact that is caused by the cart 10 being jostled during transport. The air bladder 160 may be inflated by an air compressor (not illustrated) that is in fluid communication with air bladder 160 by a supply source such as air inlet 165.

Bracket 170 may be used to secure the cushioned stabilizer 155 to a truck bed floor other surface where highly sensitive equipment on carts such as cart 10 are securely stored. Alternatively, should equipment and its associated cart require cushioned stabilizer 155 to be at a greater height in order to support the device and its cart, bracket 170 may connect the stabilizer 155 with a leg such as leg 175 illustrated in FIG. 9B, which is at a height appropriate for supporting device 15 and its associated equipment illustrated therein.

Figure 12:
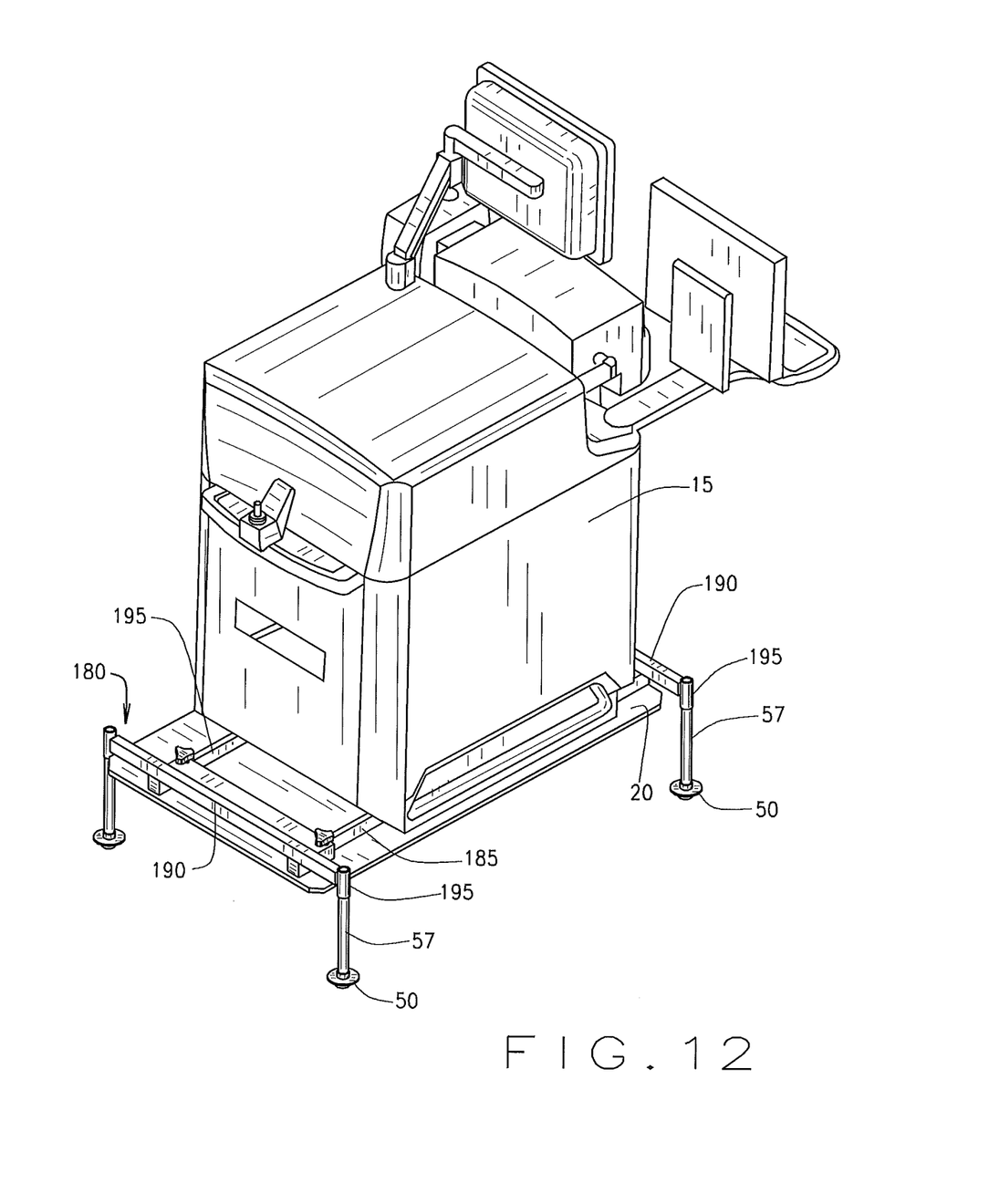
FIG. 12 illustrates a perspective view of an alternative embodiment of the modular cart of FIG. 1.

In FIG. 12 an alternative embodiment of the cart 10 from FIG. 1 is provided. In that embodiment the means by which the device 15 is attached to the interface plate 20 is different than described herein above. Instead of being mounted directly thereto adaptable interface plate 20, device 15 is mounted to rack 180. Rack 180 includes a mechanism for receiving and securing device 15 (not illustrated). Rack 180 comprises longitudinal rails 185 and latitudinal rails 190. The end portions of the latitudinal rails 190 are further attached to sleeves 195 for securing removable screw feet 50 and associated legs 57 substantially similar to those illustrated in FIG. 1. The rack 180 is attached at its top surface to device 15 and at its bottom surface to adaptable interface plate 20. In alternative embodiments, rack 180 may include attachment mechanisms for receiving and securing highly sensitive equipment other than device 15.

It should be noted that in the alternative embodiment illustrated in FIG. 12, the manner in which the interface plate 20 is associated with cart base member 40 (not illustrated) including the manual release mechanism discussed above is substantially similar to how it is described above. Moreover, the stabilizer bar 150 described in detail herein above may be further used in connection with the alternative embodiment illustrated in FIG. 12.

As is evident from the foregoing description, certain aspects of the present invention are not limited by the particular details of the examples illustrated herein, and it is therefore contemplated that other modifications and applications, or equivalents thereof, will occur to those skilled in the art. Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. A modular cart for transporting highly sensitive equipment comprising:
   a cart base member comprising a plurality of rollers;
   a sub plate selectively attachable to a top surface of said cart base member;
   an adaptable interface plate selectively attachable to a top surface of said sub plate, said adaptable interface plate comprising a plurality of apertures configured to receive and secure said highly sensitive equipment; and
   wherein said sub plate is configured to receive and secure the bottom surface of said adaptable interface plate such that the perimeter of the adaptable interface plate surrounds the perimeter of the sub plate.

2. The modular cart of claim 1 wherein the modular cart further includes a control box selectively attachable to the adaptable interface plate.

3. The modular cart of claim 1 wherein the modular cart further includes removable screw feet selectively attachable to the adaptable interface plate.

4. The modular cart of claim 3 wherein removable screw feet are in contact with a floor surface when in a down position but are not in contact with a floor surface when in the up position.

5. The modular cart of claim 1 wherein the cart base member further includes a handle attached to a pin for selective manual removal from an aperture of a frame member mounted to a floor surface.

6. The modular cart of claim 1 wherein the adaptable interface plate further includes attached thereto a stabilizer arm for selective engagement with a cushioned stabilizer mounted to a floor surface.

7. The modular cart of claim 1 wherein a rack is selectively attached to and above the adaptable interface plate and includes means for receiving the highly sensitive equipment.

8. A system for transporting highly sensitive equipment comprising:
   a modular cart comprising:
      a cart base member comprising a plurality of rollers;
      a sub plate selectively attachable to the top surface of said cart base member;
      an adaptable interface plate selectively attachable to a top surface of said sub plate, said adaptable interface plate comprising a plurality of apertures, wherein said sub plate is configured to receive and secure the bottom surface of said adaptable interface plate such that the perimeter of the adaptable interface plate surrounds the perimeter of the sub plate;
   said highly sensitive equipment selectively attachable to the plurality of apertures on the top surface of said adaptable interface plate; and
   a support frame member mounted to a floor surface for securing said modular cart, said support frame member comprising an aperture extending therethrough.

9. The system of claim 8 wherein the cart base member includes a channel for receiving the support frame member therein.

10. The system of claim 9 wherein the cart base member includes a handle attached to a pin, and wherein the aperture of the support frame member is in substantial alignment with the pin when the support frame member is received by the channel of the cart base member.

11. The system of claim 10 wherein when the handle is manually pulled outwardly, the pin is removed from the aperture of the support frame member.

12. The system of claim 8 further comprising a stabilizer arm attached to the adaptable interface plate and extending therefrom.

13. The system of claim 12 further comprising a cushioned stabilizer mounted to a floor surface, wherein the cushioned stabilizer is configured to receive the stabilizer arm.

14. A system for transporting highly sensitive equipment comprising:
   a modular cart comprising:
      a cart base member comprising a plurality of rollers;
      a sub plate selectively attachable to the top surface of said cart base member;
      an adaptable interface plate selectively attachable to a top surface of said sub plate, said adaptable interface plate comprising a plurality of apertures, wherein said sub plate is configured to receive and secure the bottom surface of said adaptable interface plate such that the perimeter of the adaptable interface plate surrounds the perimeter of the sub plate, said adaptable interface plate further comprising a stabilizer arm extending therefrom;
   highly sensitive equipment selectively attachable to the plurality of apertures on the top surface of said adaptable interface plate; and
   a cushioned stabilizer mounted to a floor surface, said cushioned stabilizer configured to receive and secure said stabilizer arm.

15. The system of claim 14 further including a support frame member mounted to a floor surface, the support frame member including an aperture extending therethrough.

16. The system of claim 15 wherein the cart base member includes a channel for receiving the support frame member therein.

17. The system of claim 16 wherein the cart base member includes a handle attached to a pin, and wherein the aperture of the support frame member is in substantial alignment with the pin when the support frame member is received by the channel of the cart base member.

18. The system of claim 17 wherein when the handle is manually pulled outwardly, the pin is removed from the aperture of the support frame member.

* * * * *